US008467863B2

(12) United States Patent
Kahlert et al.

(10) Patent No.: US 8,467,863 B2
(45) Date of Patent: Jun. 18, 2013

(54) SENSING APPARATUS FOR SENSING AN OBJECT

(75) Inventors: Joachim Kahlert, Aachen (DE); Maya Ella Barley, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 49 days.

(21) Appl. No.: 13/058,567

(22) PCT Filed: Aug. 20, 2009

(86) PCT No.: PCT/IB2009/053674
§ 371 (c)(1),
(2), (4) Date: Feb. 11, 2011

(87) PCT Pub. No.: WO2010/020958
PCT Pub. Date: Feb. 25, 2010

(65) Prior Publication Data
US 2011/0144509 A1 Jun. 16, 2011

(30) Foreign Application Priority Data
Aug. 22, 2008 (EP) .................................... 08162791

(51) Int. Cl.
*A61B 5/0428* (2006.01)
(52) U.S. Cl.
USPC ........................................................ 600/510
(58) Field of Classification Search
USPC .................... 607/62, 119, 122; 600/510, 547
See application file for complete search history.

(56) References Cited

U.S. PATENT DOCUMENTS

| | | | |
|---|---|---|---|
| 5,098,430 A | 3/1992 | Fleenor | |
| 5,147,370 A | 9/1992 | McNamara et al. | |
| 5,300,048 A | 4/1994 | Drewes, Jr. et al. | |
| 5,472,442 A | 12/1995 | Klicek | |
| 5,836,874 A * | 11/1998 | Swanson et al. | 600/374 |
| 6,063,084 A | 5/2000 | Farin | |
| 6,240,307 B1 | 5/2001 | Beatty et al. | |
| 6,603,996 B1 * | 8/2003 | Beatty et al. | 600/513 |
| 6,855,161 B2 | 2/2005 | Boylan et al. | |
| 6,892,091 B1 | 5/2005 | Ben-Haim et al. | |
| 7,194,294 B2 * | 3/2007 | Panescu et al. | 600/374 |
| 7,364,546 B2 | 4/2008 | Panescu et al. | |
| 2006/0058693 A1 | 3/2006 | Beatty et al. | |
| 2008/0312521 A1 * | 12/2008 | Solomon | 600/374 |

OTHER PUBLICATIONS

Wakhloo et al., "Self-Expanding Nitinol Stents in Canine Vertebral Arteries: Hemodynamics and Tissue Response", American Journal of Neuroradiology, 1995, 16(5): pp. 1043-1051.
Lin et al., "Validation of the Frequency Spectra Obtained from the Noncontact Unipolar Electrograms During Atrial Fibrillation", Journal of Cardiovascular Electrophysiology, 2007, 18(11): pp. 1147-1153.
Rao et al., "Global Comparisons Between Contact and Noncontact Mapping Techniques in the Right Atrium: Role of Cavitary Probe Size", Annals of Biomedical Engineering Biomed. Eng. Soc. USA, vol. 29, No. 6, Jun. 2001, pp. 493-500.

* cited by examiner

*Primary Examiner* — George Evanisko

(57) ABSTRACT

A sensing apparatus for sensing an object includes an arrangement of sensing elements for sensing a property of the object. The sensing elements are operable in a contact mode, in which a sensing is performable, while the sensing elements are in contact with the object, and in a non-contact mode, in which a sensing is performable, while the sensing elements are not in contact with the object. The sensing apparatus further includes a mode determination unit for determining whether or not a sensing element is in contact with the object.

12 Claims, 4 Drawing Sheets

SENSING APPARATUS FOR SENSING AN OBJECT

FIELD OF THE INVENTION

The present invention relates to a sensing apparatus, a sensing method and a corresponding computer program.

BACKGROUND OF THE INVENTION

U.S. Pat. No. 6,892,091 B1 discloses an apparatus and a method for generating an electrical map of a chamber of a heart, wherein a catheter is utilized including a body having a proximal end and a distal end. The distal end of the body comprises an arrangement of non-contact electrodes and a distal tip with a contact electrode. The non-contact electrodes are adapted for measuring far field electrical signals in the heart chamber, which allows determining electrical properties with a low spatial and temporal resolution only. The single contact electrode at the distal tip allows measuring the electrical properties of the heart chamber directly on the endocardial surface of the heart chamber, i.e. more accurately than by using the non-contact electrodes, but in order to acquire a map of the endocardial surface showing the electrical properties at different locations, the distal tip with the contact electrode has to be moved sequentially from location to location, which is time consuming.

SUMMARY OF THE INVENTION

It is an object of the present invention to provide a sensing apparatus, a sensing method and a corresponding computer program, wherein a map of a property of an object can be sensed more accurately and faster.

In an aspect of the present invention a sensing apparatus for sensing an object is presented, wherein the sensing apparatus comprises an arrangement of sensing elements for sensing a property of the object, wherein the sensing elements are operable in a contact mode, in which a sensing is performable, while the sensing elements are contact with the object, and in a non-contact mode, in which a sensing is performable, while the sensing elements are not in contact with the object.

The invention is based on the idea that, since the arrangement of sensing elements is operable in the contact mode and in the non-contact mode, the sensing apparatus can be used for firstly sensing a larger region of the object in a non-contact mode, wherein because of the distance to the object the accuracy of the sensing procedure is reduced in comparison to a contact sensing. The result of the non-contact sensing can then be used for determining a region of interest of the object, in which, for example, certain properties have been sensed, and the arrangement of sensing elements can be moved to this region of interest for sensing this region in the contact mode more accurately, because the same sensing elements can be used in the contact mode and in the non-contact mode, i.e. because the sensing elements are not fixed to a certain sensing mode. Thus, the sensing apparatus allows determining a property of an object in a two-step approach by using the sensing elements in the non-contact mode and in the contact mode, wherein in a first step a larger region of the object, in particular, the whole object, can be sensed roughly by the arrangement of sensing elements in the non-contact mode for determining a region of interest and wherein in a following step the determined region of interest can be sensed more accurately by the arrangement of sensing elements in the contact mode. This allows focusing the sensing procedure on a region of interest and sensing this region of interest more accurately. In particular, an accurate map of a property of the object can be determined faster than in the above described prior art by using the arrangement of sensing elements in the contact mode, wherein this accurate determination of the map can be focused to a region of interest.

The property being sensed by the sensing apparatus is preferentially an electrical property of the object like the electrical potential of the object at different locations. If the object is a heart, the determined electrical potentials form electrograms. In particular, if several electrical potentials are determined at different locations of a heart, a map of electrograms can be determined.

The sensing elements are preferentially electrodes for measuring electrical signals. It is further preferred that the sensing elements are adapted to measure the impedance of the object at a location, at which the sensing element is in contact with the object, in the contact mode.

The measured impedance of the object is preferentially measured with several sensing elements at different locations, wherein, for example, because the impedance of abnormal tissue and/or healthy tissue is known, the size of a lesion can be determined based on the measured impedance at different locations. The lesion is, for example, a lesion caused by an illness and/or by actively applying energy like during a thermal therapy or a laser ablation treatment. The sensing elements are preferentially adapted to inject a current at least one first location and to measure the injected current at least one second location for determining the impedance between the at least one first location and the at least one second location.

The sensing elements are preferentially adapted to acquire an electrical signal, which can be regarded as a property of the object or which is used for determining a property of the object, from the object, wherein the object is preferentially a heart or a part of a heart and wherein sensing apparatus preferentially further comprises an analysis unit for determining whether the electrical signal indicates abnormal behaviour of the heart or not, in particular, whether it indicates an abnormal electrogram or not. A site on the endocardial surface, on which an abnormal behavior of the heart or an abnormal electrogram is present, i.e. where the analysis unit could determine an abnormal behavior, is a location, at which an electrical activity is found that would not be found at that location in a normal, healthy heart. This electrical activity is, for example, a fractionated electrogram, a high dominant-frequency activity, an early activation, a rotor, a re-entrant circuit, an area of slow conduction, a pivot point or a site of a conduction block.

The sensing apparatus preferentially comprises further a mode determination unit for determining whether a sensing element is in contact with the object or not. This allows operating the sensing elements depending on whether they are in contact with the object or not. If, for example, the mode determination unit has determined that only a subset of the sensing elements is in contact with the object, preferentially only this subset is operated in a contact mode, whereas the other sensing elements are preferentially operated in the non-contact mode.

In an embodiment, the sensing elements are adapted for measuring the impedance of the object, in particular, if the object is a heart, of the cardiac tissue between adjacent sets of sensing elements, which are, in this case, electrodes, wherein the mode determination unit is adapted to determine significant changes in the impedance which indicate contact with the cardiac tissue, in particular, with the endocardium. For example, if two electrodes are in contact with the tissue the measured impedance is the tissue impedance of the endocardium between these two adjacent points. If one of the electrodes is not in contact with the tissue, the impedance of the blood between the two electrodes is measured. The impedance of blood differs significantly from the impedance of tissue and is preferentially used as a specific indication whether an electrode is in contact or not. The impedance of blood is roughly 20% lower than the impedance of healthy (blood perfused) tissue. Non perfused tissue, for example, dead, in particular, ablated tissue, is characterized by a lower impedance than that of normal tissue. Blood has, for example, an impedance of 150 Ω/cm, the normal endocardium has, for example, an impedance of 350 Ω/cm and scar tissue has, for example, an impedance of 100 Ω/cm.

In a further embodiment, the sensing apparatus further comprises an imaging apparatus for imaging the object and the sensing element, wherein the mode determination unit is adapted to determine the positions of the sensing elements and of the object in the image and for determining from these positions whether the sensing element is in contact with the object or not. In another embodiment, the mode determination unit is adapted to determine the position of at least one other element in the image, wherein the spatial relation of this at least one other element to the sensing element and/or to the object is known, and to determine the position of the sensing element and/or of the object from the determined position of the at least one other element, wherein the mode determination unit is adapted to determine from the determined positions of the sensing element and/or the object whether the sensing element is in contact with the object or not. In an embodiment, the positions of the different sensing elements on the arrangement of sensing elements are known and the position and orientation of the arrangement with respect to the object is determined from the image, wherein the mode determination unit is adapted to determine the positions of the sensing elements relative to the object from the determined position and orientation of the arrangement of sensing elements relative to the object and the known positions of the sensing elements on the arrangement of sensing elements, in order to determine whether a sensing element is in contact or not in contact with the object.

In a preferred embodiment, the sensing elements are adapted to determine a property of the object depending on whether the sensing element is in the contact mode or in the non-contact mode, in particular, the kind of determining a property of an object is chosen depending on whether the sensing elements are in the contact mode or in the non-contact mode. This allows adapting the determination of the property of the object to the respective mode, i.e. the contact mode or the non-contact mode.

It is further preferred that the sensing elements are adapted to acquire an electrical signal, which depends on the property to be determined, by performing a unipolar acquisition, if the sensing elements are in the non-contact mode, and to acquire an electrical signal, which depends on the electrical potential, by performing a unipolar or a bipolar acquisition, if the sensing elements are in the contact mode. Not all sensing elements have to be in the contact mode or in the non-contact mode. For example, a subset of the sensing elements can be in the contact mode only, wherein this subset of sensing elements can perform a bipolar acquisition, whereas the other sensing elements are, for example, not operated or are operated for performing a unipolar acquisition.

The sensing apparatus preferentially further comprises an electrical signal processing unit for processing the electrical signal, wherein the electrical signal processing unit is adapted to perform a non-contact mode filtering and a transformation of the filtered electrical signal to a surface of the object, at which the property of the object is to be determined, if the sensing elements are in the non-contact mode, and to perform a contact mode filtering, if the sensing elements are in the contact mode. This improves the quality of the electrical signals, which can be regarded as a property of the object or on which a determination of a property of the object is based. The filter is preferentially a low-pass filter for improving the signal quality and the noise behaviour. In contact mode, the signals are preferentially bandpass filtered to retain only frequencies between 30 and 500 Hz. In non-contact mode, the bandpass filter is preferentially from 0.1 to 300 Hz.

It is further preferred that the sensing elements are adapted to acquire an electrical signal, which depends on a property to be determined, and wherein the sensing apparatus comprises an electrical signal transformation unit for transforming the electrical signal to a surface of the object, at which the property of the object is to be determined, if the sensing elements are in the non-contact mode. If the object is a heart, the surface of the object is preferentially the endocardial surface of a heart chamber. This allows determining electrical properties on a surface of the object, even if the sensing elements are not in contact with the surface.

The transformation is preferentially performed by using known methods using Laplace's Equation, for example, the method disclosed in the article by Lin et al., Journal of Cardiovascular Electrophysiology, 2007, 18 (11): 1147-1153 or the method disclosed in the US Patent Application 2006/0058693, which are herewith incorporated by reference.

It is further preferred that the sensing apparatus further comprises a tube for containing at least the arrangement of sensing elements for guiding the sensing elements in the interior of an object for sensing the interior of the object. The tube is preferentially a catheter. The interior is preferentially a cavity, for example, of an object like a heart. In particular, the tube is preferentially a catheter for guiding the sensing elements into a heart chamber.

It is further preferred that the sensing apparatus comprises a holding structure for holding the arrangement of sensing elements, wherein the sensing elements are arranged on the holding structure, wherein the holding structure is adjustable between a folded condition and at least one unfolded condition and wherein the holding structure comprises an elongated shape in the folded condition. This allows guiding the sensing elements to an interior of an object, in particular, within a tube like a catheter more easily, because the holding structure in the elongated shape can be guided through small openings.

The holding structure has in the at least one unfolded conditions preferentially an ellipsoidal or spherical shape, wherein the sizes of ellipsoidal or spherical shapes of different unfolded conditions are preferentially different.

The sensing elements, which are preferentially electrically conductive elements like electrodes, are preferentially arranged on the holding structure such that the sensing elements are located on the outer surface of the holding structure, if the holding structure is in an unfolded condition.

In an unfolded condition, the holding structure does not have to be completely unfolded. For example, in a first unfolded condition the holding structure can be more unfolded, i.e. the degree of unfolding can be larger, than in a different second unfolded condition.

The holding structure is preferentially adapted such and the sensing elements are preferentially arranged such that the spacing between the sensing elements in a first unfolded condition is different to the spacing between the sensing elements in a second unfolded condition.

Preferentially, in a first unfolded condition the holding structure and the sensing elements are adapted such that they are able to perform a sensing of the entire left atrium of a heart in the non-contact mode, in particular, to measure electrical signals, in particular, to determine the electrical potentials and, thus, the electrograms, at different locations within the entire left atrium, with a larger spacing between the sensing elements, i.e. with a smaller spatial resolution. This first unfolded condition could be a condition, in which the holding structure is completely unfolded. In a second unfolded condition, the holding structure is preferentially less unfolded and the spacing between the sensing elements is reduced. In this second unfolded condition, the electrical signals, in particular, the electrical potentials, are preferentially determined in the contact mode, wherein the spatial resolution is increased because of the smaller spacing of the sensing elements. This allows determining roughly regions within the left atrium or another part of the heart, at which an abnormal behavior, in particular, an abnormal electrogram, could be present, in the non-contact mode in the first unfolded condition and then determining more precisely at these regions the electrical signals, in particular, the electrograms, in the contact mode in the second unfolded condition.

The sensing elements are preferentially adapted to apply energy and to receive energy. This allows sensing the object by receiving energy like, for example, electrical energy for determining an electrical potential, and treating the object by applying energy using the same sensing element, wherein the size of an apparatus for sensing and applying energy can be reduced and the influence of the application of energy can easily be monitored at the location, at which the energy has been applied. Furthermore, if the object is a heart, this allows sensing and stimulating like in pacing catheters. This is especially useful if a cardiologist wishes to simulate ectopic foci during ablation, of if the cardiologist wishes to delineate the borders of an underlying ganglionated plexi, which can be done by pacing the cardiac tissue and measuring the local change in the R-R interval.

The sensing apparatus preferentially comprises markers for being visualized in an imaging apparatus. This allows localizing the sensing apparatus within an object, for example, within a heart chamber.

The markers can be the sensing elements and/or the holding structure, i.e. a single element can function as, for example, a sensing element and/or holding structure, and as a marker.

The imaging apparatus is preferentially an X-ray imaging apparatus, in particular, an X-ray fluoroscopy apparatus. In other embodiments, the imaging apparatus is, for example, a magnetic resonance imaging apparatus, an optical imaging apparatus, a nuclear imaging apparatus or an acoustical imaging apparatus.

The sensing apparatus preferentially further comprises a registering unit for registering the sensing elements and a model of the object. This allows determining at which location of the object a sensing element is located and/or at which location of the object an electrical signal has been determined by indicating the corresponding positions on the model.

The model of the object is, for example, a two- or three-dimensional model of the object being an image of the object generated by the imaging apparatus or being based on such an image by, for example, adapting the model to the image. The model can also be a model of a moving object like a heart or a part of a heart, i.e. the model is, in an embodiment, a four-dimensional model.

If the analysis unit has determined areas of abnormal electrograms, these areas can be indicated and visualized on a display unit showing a representation of the object, in particular, a model of the object, which is preferentially a heart or a heart chamber, wherein these areas are indicated on this representation. The model is preferentially a model of the kind described above, wherein the model and the sensing elements can be registered using an image showing the object and the sensing elements or showing markers attached to the object and/or the sensing elements.

The sensing apparatus further comprises a steering unit for steering the sensing element to a region within an object, in particular, within a heart chamber. The steering unit can be adapted for steering the sensing element manually and/or the steering unit can comprise a robotic system for robotically steering the sensing element. This allows steering the sensing element, in particular, the holding structure in the unfolded condition, to a desired region within the object, in particular, at an endocardial surface of a heart chamber.

In a further aspect of the present invention a sensing method for sensing a property of an object is presented, the sensing method comprising the steps of:

sensing the property of the object by using an arrangement of sensing elements, while the sensing elements are not in contact with the object, in a non-contact mode, sensing the property of the object by using the arrangement of sensing elements, while the sensing elements are in contact with the object, in a contact mode.

The sensing method preferentially further comprises following steps after the sensing in the non-contact mode and before the sensing in the contact mode:

determining a region of interest of the object based on the property sensed in the non-contact mode, bringing the sensing element into contact with the object in the region of interest.

In further aspect of the present invention a computer program for sensing an object is presented, wherein the computer program comprises program code means for causing the sensing apparatus to carry out the steps of the sensing method, when the computer program is run on a computer controlling the sensing apparatus.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
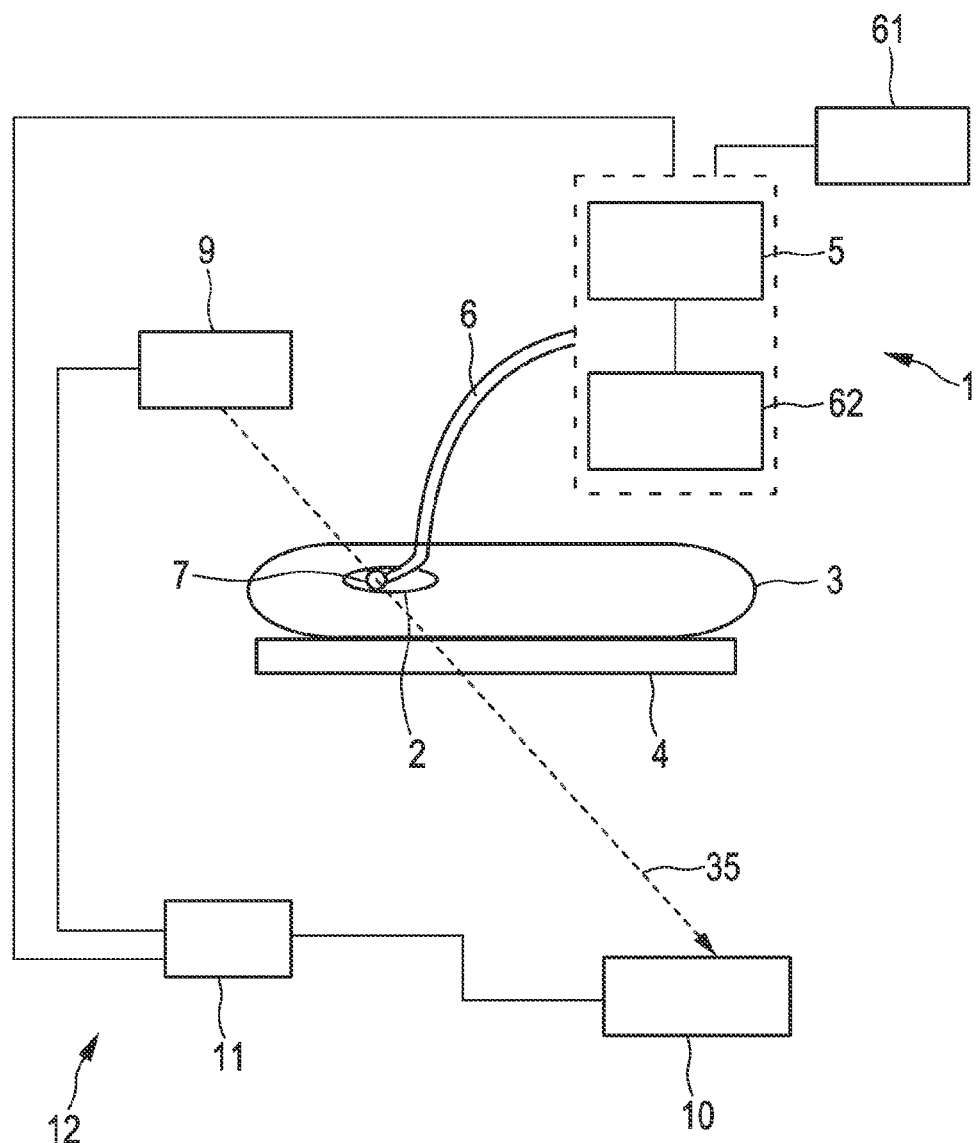
FIG. 1 shows schematically and exemplarily a representation of an embodiment of a sensing apparatus for sensing an object in accordance with the invention.

FIG. 1 shows an apparatus 1 for sensing an object. The apparatus 1 comprises a tube, in this embodiment a catheter 6, and an arrangement 7 of sensing elements for sensing a property of the object. At least some sensing elements of the arrangement 7 are operable in a contact mode, in which a sensing is performable, while the sensing elements are in contact with the object, and in a non-contact mode, in which a sensing is performable, while the sensing elements are not in contact with the object, i.e. the same sensing elements can be operated in the contact mode and in the non-contact mode.

The arrangement 7 of sensing elements is connected to a control unit 5 via the catheter 6. The catheter 6 with the arrangement 7 of sensing elements can be introduced into an object 2, which is, in this embodiment, a heart of a patient 3 located on a patient table 4, wherein the catheter 6 is steered and navigated to the heart chambers by a steering unit 62 using built-in guiding means (not shown). In another embodiment, the steering unit 62 can comprise an introducer for steering and navigating the catheter 6 to guide the catheter 6 passively into the object 2. The steering unit 62 can be adapted for steering the arrangement 7 of sensing elements manually and/or the steering unit 62 can comprise a robotic system for robotically steering the arrangement 7 of sensing elements. This allows steering the arrangement 7 of sensing elements to a desired region within the object, in particular, at an endocardial surface of a heart chamber.

Figure 2:
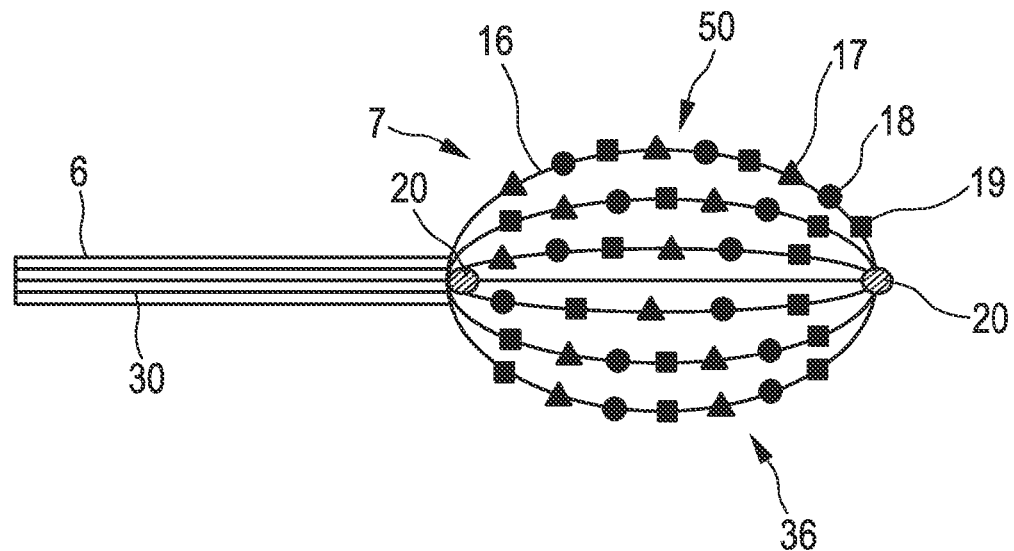
FIG. 2 shows schematically and exemplarily sensing elements on a holding structure of the embodiment of the sensing apparatus in an unfolded condition.

The dashed box in FIG. 2 indicates that both, the control unit 5 and the steering unit 62, are coupled to the catheter 6 comprising the arrangement 7 of sensing elements.

During introduction of the arrangement 7 and the catheter 6 into the object 2 an imaging apparatus 12, which is in this embodiment a fluoroscopy device, generates images of the object 2 and the arrangement 7. This imaging device 12 preferentially generates images of the object 2 and the arrangement 7, also if the arrangement 7 is already located within the object 2.

In other embodiments, the object can, for example, be another hollow organ of a patient or a technical object, in particular, a hollow technical object, whose inner surface has to be sensed.

The imaging apparatus 12, i.e. in this embodiment the fluoroscopy device 12, comprises an X-ray source 9 and a detection unit 10, which are controlled by a fluoroscopy control unit 11. The fluoroscopy device 12 generates X-ray projection images of the object 2 and of the arrangement 7 in a known way. The X-rays of the X-ray source 9 are schematically indicated by the arrow 35.

In another embodiment, instead of a fluoroscopy device, another imaging apparatus can be used for generating an image comprising the object 2 and the arrangement 7. For example, a magnetic resonance imaging device, an ultra sonic imaging device or a computed tomography imaging device can be used for generating an image of the object 2 and the arrangement 7.

An embodiment of an arrangement 7 of sensing elements 17 and a catheter 6 is schematically shown in more detail in FIG. 2. The arrangement 7 is held on a holding structure 50, which is adjustable between a folded condition and at least one unfolded condition. The holding structure 50 comprises an elongated shape in the folded condition, which is schematically and exemplarily shown in FIG. 3 and which allows to introduce the arrangement 7 into the object 2. In FIG. 2, the holding structure 50 comprising the sensing elements 17 is shown in an unfolded condition. The holding structure 50 is adapted such and the sensing elements 17 are arranged such that the spacing between at least some of the sensing elements 17 in a first unfolded condition is different to the spacing between the sensing elements in a second unfolded condition.

In the embodiment shown in FIG. 2, the holding structure 50 further holds energy emission elements 19 and another kind of sensing elements 18. For example, the sensing elements 17 can be electrodes for measuring an electrical signal for determining an electrical potential, whereas the sensing elements 18 can be temperature sensors for measuring the temperature of the object. At least the sensing elements 17 are operable in the contact mode and in the non-contact mode. The further kind of sensing elements 18 and/or the energy emission elements 19 can be omitted in another embodiment, i.e. in an embodiment the arrangement 7 only comprises the sensing elements 17, which are operable in the contact mode and in the non-contact mode.

The sensing elements 17 are electrodes preferentially adapted to measure an electrical property of the object 2 like the electrical potential of the object 2 at different locations. If the object is a heart, the determined electrical potentials form electrograms, wherein, since several electrical potentials are determined at different locations of a heart, a map of electrograms can be determined.

The sensing elements 17 are adapted to determine a property of the object 2 depending on whether the respective sensing element 17 is in the contact mode or in the non-contact mode, in particular, the kind of determining a property of an object is chosen depending on whether the respective sensing element 17 is in the contact mode or in the non-contact mode. This allows adapting the determination of the property of the object to the respective mode, i.e. the contact mode or the non-contact mode. In this embodiment, the sensing elements 17 are adapted to acquire an electrical signal, which depends on or is the property to be determined, by performing a unipolar acquisition, if the sensing elements 17 are in the non-contact mode, and to acquire an electrical signal, which depends on the electrical potential, by performing a bipolar acquisition, if the sensing elements 17 are in the contact mode. Not all sensing elements 17 have to be in the contact mode or in the non-contact mode. For example, a subset of the sensing elements 17 can be in the contact mode only, wherein this subset of sensing elements 17 can perform a bipolar acquisition, whereas the other sensing elements 17 are, for example, not operated or are operated for performing a unipolar acquisition.

In an embodiment, the sensing elements 17 are adapted to apply energy and to receive energy. This allows sensing the object by receiving energy like, for example, electrical energy for determining an electrical potential, and treating the object by applying energy using the same sensing element, wherein the size of an apparatus for sensing and applying energy can be reduced and the influence of the application of energy can easily be monitored at the location, at which the energy has been applied. Especially in this case, the further kind of sensing elements 18 and/or the energy emission elements 19 can be omitted. Furthermore, if the object 2 is a heart, this allows sensing and stimulating like in pacing catheters. This is especially useful if a cardiologist wishes to simulate ectopic foci during ablation, or if the cardiologist wishes to delineate the borders of an underlying ganglionated plexi, which can be done by pacing the cardiac tissue and measuring the local change in the R-R interval.

The holding structure 50 has in the at least one unfolded conditions preferentially an ellipsoidal or spherical shape, wherein the dimensions of ellipsoidal or spherical shapes of different unfolded conditions are preferentially different.

The sensing elements 17, which are electrically conductive elements like electrodes in this embodiment, are arranged on the holding structure 50 such that the sensing elements 17 are located on the outer surface 36 of the holding structure 50, if the holding structure 50 is in an unfolded condition.

In an unfolded condition, the holding structure 50 does not have to be completely unfolded. For example, in a first unfolded condition the holding structure 50 can be more unfolded, i.e. the degree of unfolding can be larger, than in a different second unfolded condition.

The holding structure 50 is adapted such and the sensing elements 17 are arranged such that the spacing between the sensing elements 17 in a first unfolded condition is different to the spacing between the sensing elements 17 in a second unfolded condition.

In this embodiment, in a first unfolded condition the holding structure 50 and the sensing elements 17 are adapted such that they are able to perform a sensing of the entire left atrium of a heart 2 in the non-contact mode, in particular, to determine electrical signals, in particular, the electrical potentials and, thus, the electrograms, at different locations within the entire left atrium, with a larger spacing between the sensing elements, i.e. with a smaller spatial resolution. This first unfolded condition is, for example, a condition, in which the holding structure 50 is completely unfolded. In a second unfolded condition, the holding structure 50 is less unfolded and the spacing between the sensing elements 17 is reduced. In this second unfolded condition, the electrical signals, in particular, the electrical potentials, are determined in the contact mode, wherein the spatial resolution is increased because of the smaller spacing of the sensing elements 17. This allows determining roughly regions within the left atrium or another part of the heart 2, at which an abnormal behavior, in particular, an abnormal electrogram could be present, in the non-contact mode in the first unfolded condition and then determining more precisely at these regions the electrical signals, in particular the electrograms, in the contact mode in the second unfolded condition.

The holding structure 50 comprises a basket made of several splines 16, which comprise the sensing elements 17 (indicated by triangles) and, in this embodiment, the energy emission elements 19 (indicated by squares) and the further kind of sensing elements 18 (indicated by circles). The distribution of the sensing elements 17, 18 and the energy emission elements 19 is only schematically and exemplarily in FIG. 2 and does not limit the invention to a certain distribution. Preferentially, the sensing elements 17 and also possible further sensing elements 18 and energy emission elements 19 are evenly distributed along the splines 16 and along the abutting surface 36.

In the unfolded condition, which is shown in FIG. 2, the holding structure 50 forms substantially an ellipsoid or a sphere. Thus, in the unfolded condition, the outer surface 36 is preferentially a surface of an ellipsoid or a sphere. For sensing the object 2 in the contact mode and/or for applying energy to the object 2, the outer surface 36 preferentially abuts against a surface of the object 2 such that the positions of the sensing elements 17, 18 and the energy emission elements 19 remain unchanged relative to the surface of the object 2 during the sensing procedure and during a possible energy application procedure. These fixed positions of the sensing elements 17, 18 and the energy emission elements 19 relative to the object surface are preferentially achieved by elastics properties of the splines 16 and, therefore, of the holding structure 50. This elasticity of the splines 16 results in an elastic force, which presses the sensing elements 17, 18 and the energy emission elements 19 against the object surface. The elasticity of the splines 16 also allows conforming of the outer surface 36 to the object surfaces and following a motion of the object 2, while the sensing elements 17, 18 and the energy emission elements 19 are continuously in contact with the object surface, or, in other embodiments, the distance between these elements 17, 18, 19 to the object surface remains continuously constant, even if the object 2 moves.

Figure 3:
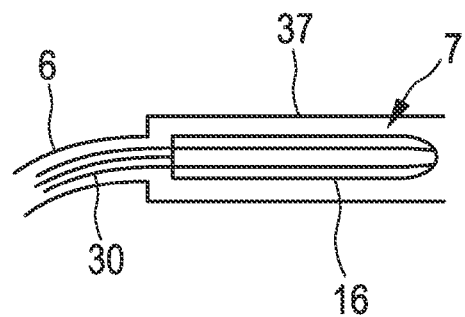
FIG. 3 shows schematically and exemplarily the sensing elements with the holding structure in a folded condition.

The splines 16 comprise preferentially wires made of a memory alloy. In this embodiment the splines 16 are made of nitinol. For unfolding the arrangement 7, i.e. for unfolding of the holding structure 50, the memory effect of the nitinol is used. The nitinol wires are pre-shaped and elastic as a spring. In the folded condition, which is schematically shown in FIG. 3 and in which the arrangement 7 takes a smaller space, the splines 16 of the arrangement 7 are located within a catheter shaft 37, in particular, in a small pipe within the catheter shaft 37. For unfolding the arrangement 7, i.e. for changing from the folded condition to the unfolded condition, the splines 16 are moved out of the catheter shaft 37, wherein the arrangement 7 forms the outer surface 36 because of the memory effect of the nitinol wires.

FIG. 3 is a schematic view only. In order to enhance the clarity of the folded condition, the illustration shows only some splines 16 of the arrangement 7 and sensing or energy emission elements are not shown, although they are still present.

Figure 4:
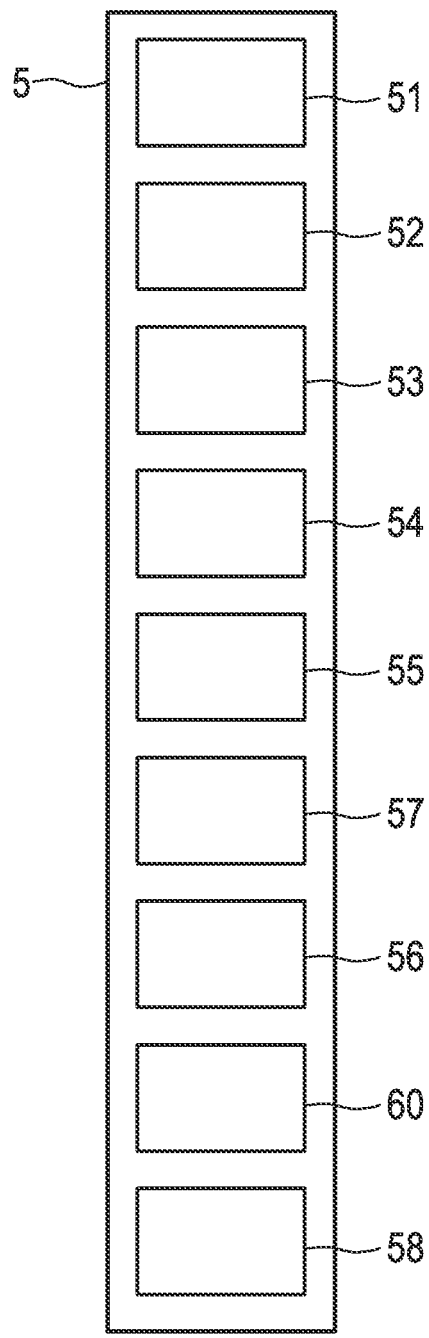
FIG. 4 shows schematically and exemplarily a control unit of the embodiment of the sensing apparatus and FIG. 5 shows exemplarily a flow chart illustrating an embodiment of a sensing method for sensing an object in accordance with the invention.

The control unit 5 comprises several further units, which are exemplarily and schematically shown in FIG. 4.

The control unit 5 comprises an electrical signal detection unit 51, which is connected via lines 30 with the sensing elements 17, in order to measure an electrical signal. The lines, which connect the electrical signal detection unit 51 with the sensing elements 17 are preferentially wires. The control unit 5 further comprises an electrical energy application unit 52, which is, in this embodiment, also connected to the sensing elements 17 via the lines 30 in order to allow the sensing elements 17 to apply electrical energy to the object 2. Thus, in this embodiment, the sensing elements 17 are able to detect electrical signals and to apply electrical energy.

The control unit 5 also comprises a temperature detection unit 53 for detecting the temperature sensed by the further sensing elements 18, which are connected with the temperature detection unit 53 via electrical conductors, in particular, via wires. If, in an embodiment, the sensing elements 18 are not present, the control unit 5 preferentially does not comprise the temperature detection unit 53. An optical energy application unit 54 is connected to the energy emission elements 19 for applying optical energy to the object 2. Preferentially, the optical energy application unit 54 is connected to the energy emission elements 19 via optical fibres. If, in an embodiment, the sensing apparatus does not comprise the energy emission elements 19, the control unit 5 does preferentially not comprise the optical energy application unit 54, which includes preferentially a laser. The optical energy application unit 54 and the energy emission elements 19 can be adapted for performing an ablation procedure, in particular, in a heart chamber.

The control unit 5 further comprises a mode determination unit 55 for determining whether a sensing element 17 is in contact with the object 2 or not. This allows operating the sensing elements 17 depending on whether they are in contact with the object 2 or not. If, for example, the mode determination unit 55 has determined that only a subset of the sensing elements 17 is in contact with the object 2, only the subset is operated in a contact mode, whereas the other sensing elements are preferentially operated in the non-contact mode.

For determining the mode of the sensing elements 17, the sensing elements 17 and the electrical signal detection unit 51 are adapted for measuring the impedance of the object, which is preferentially a heart, between adjacent sensing elements 17, which are, as already mentioned above, in this embodiment, electrodes. The mode determination unit 55 is adapted for determining significant changes in the impedance which indicate contact with the object, in particular, with the endocardium. Thus, by detecting these significant changes in the impedance, it is determined whether the respective sensing element 17 is in contact with the object 2 or not.

In another embodiment, the imaging apparatus 12 images the object 2 and the sensing element 17 and the mode determination unit 55 is adapted to determine the positions of the sensing elements 17 and of the object 2 in the image, wherein the mode determination unit 55 determines from these positions whether the respective sensing element 17 is in contact with the object 2 or not. The mode determination unit 55 can also be adapted to determine the position and orientation of the arrangement 7 of sensing elements 17 with respect to the object 2 from the image and to determine from the position and orientation the positions of the sensing elements 17, if the locations of the sensing elements 17 on the arrangement 7 are known, for determining whether the respective sensing element 17 is in contact with the object 2 or not.

The control unit 5 further comprises an electrical signal processing unit 57 for processing electrical signals detected by the electrical signal detection unit 51 and the sensing elements 17.

The electrical signal processing unit 57 is adapted to perform a non-contact mode filtering of the electrical signal received from the electrical signal detection unit 51, if the mode determination unit 55 has detected that the respective sensing element 17 is not in contact with the object 2. In this embodiment, the filter used for the filtering in the non-contact mode is a low-pass filter retaining frequencies preferentially from 0.1 to 300 Hz, further preferred from 1 to 200 Hz and further preferred from 50 to 150 Hz.

The electrical signal processing unit 57 is further adapted to perform a contact mode filtering of the electrical signal received from the electrical signal detection unit 51, if the mode determination unit 55 has detected that the respective sensing element 17 is in contact with the object 2. In this embodiment, the filter used for the filtering in the contact mode is a low-pass filter retaining frequencies preferentially from 30 to 500 Hz, further preferred from 100 to 400 Hz and further preferred from 200 to 300 Hz.

If the mode determination unit 55 has detected that a sensing element 17 is in the non-contact mode, the electrical signal acquired via this sensing element 17 is transformed to a surface of the object 2, at which the property like, for example, the electrical potential, of the object has to be determined, by an electrical signal transforming unit 56. In this embodiment, in the non-contact mode, the respective sensing element acquires electrical signals by performing a unipolar acquisition, wherein an electrical signal is detected, which emanates from an endocardial surface and travels through the blood. The electrical signal transforming unit 56 is adapted to reconstruct the electrical signals, in particular, the electrical potentials on the endocardial surface by solving an inverse problem, which describes the relation between the electrical signals on the endocardial surface and the electrical signals measured in the non-contact mode. The electrical transforming unit 56 is preferentially adapted to perform this transformation, i.e. to solve the inverse problem, by using Laplace's Equation, in particular, by using the method disclosed in the article by Lin et al., Journal of Cardiovascular Electrophysiology, 2007, 18 (11): 1147-1153 or the method disclosed in US 2006/0058693, which are herewith incorporated by reference.

Thus, the mode determination unit 55 detects whether the respective sensing element 17 is in contact with the object 2 or not, i.e. whether the respective sensing element 17 is in the contact mode or in the non-contact mode, the electrical signal processing unit 57 processes the electrical signal received from the electrical signal detection unit 51 depending on whether the respective sensing element 17 is in the contact mode or in the non-contact mode, and the electrical signal transforming unit 56 transforms the electrical signals onto the endocardial surface, if they have been acquired in the non-contact mode.

Furthermore, also the acquisition of the electrical signals by using the sensing elements 17 and the electrical signal detection unit 51 depends on the detection of the mode determination unit 55, i.e. depends on whether the respective sensing element 17 is in the contact mode or in the non-contact mode. If the respective sensing element 17 is in the contact mode, i.e. if the respective sensing element 17 is in contact with the object 2, the electrical signal detection unit 51 and the respective sensing element 17 perform preferentially a bipolar acquisition, whereas, if the respective sensing element 17 is not in contact with the object 2, i.e. if the respective sensing element 17 is in the non-contact mode, the electrical signal detection unit 51 and the respective sensing element 17 perform a unipolar acquisition of electrical signals.

The control unit 5 further comprises an analysis unit 60 for analyzing whether electrical signals, which have been detected by the electrical signal detection unit 51, processed by the electrical signal processing unit 57 and, in the non-contact mode, transformed by the electrical signal transformation unit 56, indicate an abnormal behavior of the heart or not, in particular, whether they indicate an abnormal electrogram or not. A site on the endocardial surface, on which an abnormal behavior of the heart or an abnormal electrogram is present, is a location, at which an electrical activity is found that would not be found at that location in a normal, healthy heart. This electrical activity is, for example, a fractionated electrogram, a high dominant-frequency activity, an early activation, rotors, re-entrant circuits, a slow conduction, a pivot point and a site of a conduction block.

In an embodiment, the analysis unit 60 is adapted to determine an early electrical activation at the endocardial surface of the heart chamber by using the electrical signal detected by the electrical signal detection unit 51, processed by the electrical signal processing unit 57 and, in the non-contact mode, transformed by the electrical signal transformation unit 56. The electrical signals caused by the electrical activation of the myocard are running as electrical waves across the endocardial surface. These waves give rise to an electrical field inside the blood-filled heart cavity that may be sensed in non-contact mode, for determining the location of the waves on the endocardial surface by using the above described transformation. Alternately, in contact mode, the electrodes on the sensing device record the passing of a wavefront in the tissue under them by sensing a change in voltage, and thus localize the wavefront. The location of the wavefront at a given point in time for a healthy heart with respect to the fundamental stimulation period is known, for example, from measurements with healthy hearts, i.e. the expected arrival time for a healthy heart is known. If the electrical signal arrives at a location earlier than expected, an early electrical activation can be determined by the analysis unit 60, which indicates an abnormal behaviour of the heart.

Furthermore, the analysis unit 60 can be adapted to determine the speed and direction of the wavefront travelling across the endocardial surface. Since at different locations electrical signals on the endocardial surface of the heart have been measured, the direction and the speed of the running wave can be calculated. The analysis unit 60 can further be adapted to determine at which location a running wave has been started from the calculated direction and the velocity. The speed and direction is, for example, calculated by the quotient of difference of arrival time and physical distance between two locations on the endocardial surface. The analysis unit 60 is preferentially further adapted to compare the determined velocity and direction and, in particular, also the location, at which the running wave started, with the corresponding velocity, direction and location, at which the running wave started, of a healthy heart, for determining whether a heart shows a normal or an abnormal behavior.

Alternatively or in addition, the analysis unit 60 can be adapted to determine an abnormal behavior, in particular, an abnormal electrogram, in a region, if at a region high dominant frequencies as disclosed in, for example, Journal of Cardiovascular Electrophysiology, 2007, 18 (11): 1147-1153, by Lin et al., are present. Furthermore, regions with chaotic or unusual electrical activity, i.e. which differs from the known normal electrical activity, can be determined as regions comprising an abnormal behavior, in particular, comprising abnormal electrograms.

Alternatively or in addition, the analysis unit 60 is adapted to determine whether the heart shows a normal or abnormal behavior based on the level of fractionation of a local electrogram in a region. A determination of the level of fractionation, which is preferentially used by the analysis unit 60, is preferentially performed as described in the article "Prospective Study of Atrial Fibrillation Termination During Ablation Guided by Automated Detection of Fractionated Electrograms" by Porter et al., Journal of Cardiovascular Electrophysiology 19(6): 613-620. This determination is preferentially performed in the time-domain by measuring signal amplitudes and time delays in a short (e.g. 2.5 second) time window of measured data.

A registration unit 58 registers the sensing elements 17 and a model of the object 2 by using an image generated by the imaging apparatus 12, in order to indicate at which locations on the object the properties have been determined. The determined properties and/or the sensing elements 17 can be shown on the model of the object 2 on a display unit 61. In particular, suspicious regions on a surface of the object 2 can be indicated on the model of the object 2 on the display unit 61. If the object 2 is a heart, a suspicious region is, for example, a region which comprises an abnormal behavior, in particular, an abnormal electrogram. Thus, in an embodiment, a region of an abnormal behavior, which is, for example, an early electrical activation or a fractionated electrogram, is shown on the model of the object 2 on the display unit 61.

The registration by the registration unit 58 is preferentially performed by using markers 20, which are visible in an image of the imaging apparatus 12. In this embodiment, the markers 20 are located at the distal tip of the holding structure 50 and at the opposite end of the holding structure 50, which is adjacent to the catheter 6.

In another embodiment, in addition or instead of the markers 20, the sensing element 17 and/or the holding structure 50 can be used as markers, if they are visible in an image of the imaging apparatus. The display unit 61 can be adapted to show also the markers on a model of the object 2.

The electrical signal detection unit 51, the connection between the electrical detection unit 51 and the sensing elements 17, and the sensing elements 17 are adapted such that each sensing element 17 is individually addressable. Preferentially, also the further kind of sensing elements 18 and the energy emission elements 19 are independently addressable.

The registration unit 58 is preferentially adapted to calculate the position of each sensing element 17 according to a coordinate system of the heart chamber being registered by using an image of the imaging apparatus 12. In an embodiment, the imaging apparatus is a three- or four-dimensional imaging modality, i.e. a modality generating a three- or four-dimensional image, and the registration is based on these three- or four-dimensional images.

The sensing apparatus 1 can be regarded as a mapping device, which combines non-contact and contact mapping into a single tool.

Although in the above described embodiment, the holding structure is spherical or ellipsoidal, the holding structure can be of any size and any three dimensional shape. The basket structure can be manufactured from a memory-shape alloy such as Nitinol (nickel-titanium), a biocompatible material that is well-known in the prior art for use in stents and other medical devices, which are, for example, disclosed in Wakhloo et al., American Journal of Neuroradiology, 1995, 16 (5):1043-1051 and in U.S. Pat. No. 5,147,370. Alternatively, the basket could be manufactured from a non-memory shape alloy (e.g. stainless steel) or polyurethane.

The basket, i.e. the holding structure 50 with the arrangement 7, is preferentially guided into the heart via a sheath threaded up through the femoral or subclavian vein, and is preferentially introduced (if necessary) into the left atrium by transeptal puncture. The basket is then deployed, i.e. unfolded, in the chamber of interest. The method by which the basket is deployed will depend on its material. The device may be pushed out of a hollow tube and assume its shape automatically (if it is composed of nitinol), as described above. Alternatively, an inflatable balloon can be used to push the splines into position.

The sensing apparatus, in particular, the sensing elements, the holding structure or the catheter are preferentially visible on the imaging apparatus (e.g. MRI-opaque for MRI visualization or radiopaque for x-ray visualization). To be radiopaque, markers of platinum, platinum/iridium, pure iridium, gold or tungsten can be attached at locations on the basket structure. If necessary, the basket, i.e. the holding structure, itself can be made more radiopaque—depending on its material—by adding an element (iridium, platinum, gold, rhenium, tungsten, palladium, rhodium, tantalum, silver, ruthenium, or hafnium) to the nitinol alloy, as, for example, disclosed in U.S. Pat. No. 6,855,161, which is herewith incorporated by reference, or by adding 20 weight percent of barium sulfate or 33.5 weight percent of bismuth subcarbonate to the polyurethane material, as disclosed in U.S. Pat. No. 5,300,048, which is herewith incorporated by reference. Stainless steel, which may also be used as a basket catheter material, i.e. as a holding structure material, is already highly-opaque.

Markers on the holding structure and/or the catheter to localize and orient the holding structure and/or the catheter on a fluoroscopy image are preferentially highly visible on imaging (e.g. MRI-opaque for MRI visualization or radiopaque for x-ray visualization e.g. composed of platinum, platinum/iridium, pure iridium, gold or tungsten). One marker is preferentially placed on each end of the basket (for localization and orientation identification), and two or more markers on the basket itself (for rotational position identification). These markers are preferentially distinguishable either by shape/size or degree of radiopacity.

The sensing elements are preferentially electrically conductive elements, i.e. electrodes, for receiving electrical signals. When the electrodes are not in contact with the endocardium, i.e. if they are in the non-contact mode, they will pick up far-field electrical signals. If at least a subset of the catheter electrodes is brought into contact with the endocardium, these electrodes will record local electrical signals (or "electrograms") from the nearby cardiac tissue. Which electrodes are in contact with the endocardium can be determined by the mode determination unit 55 by detecting changes in the characteristics of the recorded electrical signals e.g. their amplitude, signal shape, signal frequency et cetera. For example, the characteristics of the electrical signals might be known for an electrode being in contact with the object and for an electrode not being in contact with the object, wherein by comparing the actual characteristics of the electrical signals with the known characteristics it can be determined whether the respective electrode is in contact with the object or not. Alternatively or in addition, which electrodes are in contact can be determined by injecting low-amplitude currents between subsets of electrodes to measure the impedance between them. Electrodes not in contact with the endocardium have lower impedance between them, since blood is significantly more electrically conductive than heart tissue.

In non-contact mode, by post-processing the recorded signals and by calculating the position of each sensing element according to a coordinate system of the heart chamber, the electrical signals on the endocardial surface can be calculated. This is preferentially performed by using methods that are well-defined in the prior art to solve Laplace's Equation and which are disclosed in, for example, the above mentioned article by Lin et al. and in the US Patent Application 2006/0058693. Although this information gives the user real-time information on the electrical activity in the entire cardiac chamber, this information is generally not at the accuracy that is needed for ablation delivery. Therefore, instead, from the information collected in the non-contact mode, the catheter is steered manually to "high-risk" sites on the endocardial surface and brought into contact with the endocardium for a dense and accurate electrical mapping of the tissue substrate. These sites are marked on the display unit 61 that indicates their relative anatomical locations and preferentially at least one aspect of their electrical characteristics like the signal amplitude or shape. After mapping, the catheter is moved away from the endocardial surface, and the non-contact mode is used to determine changes in the cardiac activation pattern or to find new (perhaps previously hidden) abnormal electrogram regions (AERs). The next focus region is then selected, the arrangement 7 moved into contact with this region on the endocardial surface, and the process of mapping conducted again. The display unit 61 is marked with all sites recommended for ablation. An ablation catheter is then inserted, and guided to each point in turn for rapid and accurate ablation. Once all sites have been ablated, if an atrial fibrillation has organized into Atrial Tachycardia (AT) or sinus rhythm, the procedure is terminated. Otherwise, a non-contact map is again generated and further mapping is conducted. If the arrangement 7 itself comprises energy emission elements 19 as described above and/or if the sensing elements 17, i.e. the electrodes in this embodiment, are adapted to apply energy to the object, the arrangement 7 of the sensing apparatus can be used for ablation.

In an embodiment, each sensing electrode, i.e. each sensing element, (or an additional ablation electrode directly adjacent to the sensing electrode) is able to deliver ablative energy. If RF energy is to be used, this requires that the electrical connections within the basket are able to sustain high-energy, high-frequency electrical activity (as is already done in all ablation catheters, which can typically sense, stimulate and ablate from the same tip electrode). If laser ablation is to be used, fiber optic wires are preferentially used to direct laser light to the positions of each sensing electrode for delivery at the same sites or close to the sites as those at which sensing was conducted.

In a further embodiment, the analysis unit 60 is adapted to automatically detect "high-risk" areas of the endocardial surface when the sensing elements are in non-contact mode, by first processing the raw electrical signals collected to calculate electrical activity on the endocardial surface, and then post-processing this information to draw conclusions on local electrical characteristics. High risk areas in need of contact mapping may be sites of earliest activation or AERs. AERs may be sites with high dominant frequencies, zones of slow conduction, or regions with chaotic or unusual electrical activity. These high risk areas can be mapped onto a three- or four-dimensional representation of the heart chamber, for example, by using the registration unit 58.

In a further embodiment, the analysis unit 60 is adapted to automatically detect "high-risk" areas of the endocardial surface when the catheter is in contact mode, by first processing the raw electrical signals collected at the endocardial surface, and then post-processing this information to draw accurate conclusions on local electrical characteristics. The early electrical activation at the endocardial surface of the heart chamber can be detected, where the sensing elements are located, by looking automatically for the point of earliest electrical activation on the grid of electrodes in contact with the endocardial surface. The analysis unit can also be adapted to calculate the direction and the velocity of an electrical wave that is travelling across the endocardial surface by looking at "time of arrival" of an electrical signal at each of the electrodes on the grid of basket electrodes in contact with the endocardium. The analysis unit can also be adapted to automatically determine the degree of fractionation of the electrical signal at each electrode in contact with the endocardium. This electrical information can be mapped onto a three- or four-dimensional representation of the heart chamber, preferably acquired by an imaging modality, i.e. onto a three- or four-dimensional model of the heart chamber.

In a further embodiment, post-ablation the tissue impedance under the sensing elements is measured and the analysis unit calculates from the magnitude of this impedance the spatial size of the lesion created. This is preferentially performed by the sensing elements, which form preferentially a grid, wherein the impedance is measured between different sensing elements, in particular, between adjacent sensing elements. A lesion is indicated by impedance being larger than the impedance of the impedance of healthy tissue. The border of a lesion can therefore be measured by decreased impedance between two adjacent sensing elements.

In a further embodiment, the steering unit comprises a robotic system like the Hansen or Stereotaxis systems for steering the arrangement of sensing elements to any region at the endocardial surface of a heart chamber.

The sensing apparatus is preferentially adapted for a guided atrial fibrillation ablation in an electrophysiology laboratory.

The above described embodiments of the sensing apparatus, which are not only adapted for sensing a property of the object, but also for applying energy to the object, can be regarded as an energy application apparatus.

Figure 5:
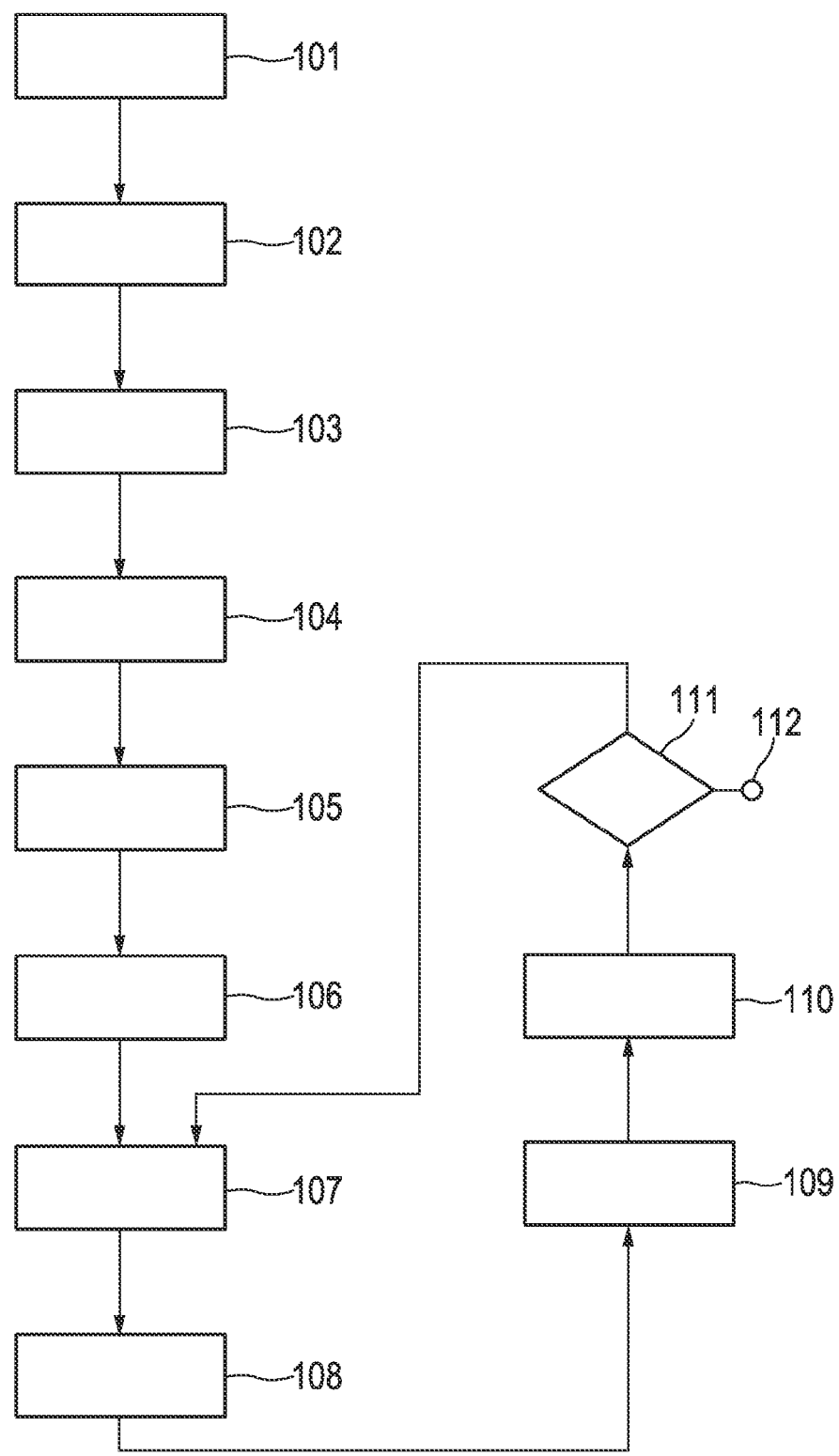

In the following an embodiment of a sensing method will be exemplarily described with reference to a flow chart shown in FIG. 5.

The arrangement 7 of the sensing elements 17 has been introduced into the object 2, which is, in this embodiment, a heart of a patient, while the holding structure 50 is in the folded condition using the catheter 6. In step 101, the holding structure 50 is changed to an unfolded condition, and in step 102 far-field electrical signals are acquired by the sensing elements 17 using a unipolar acquisition, while the sensing elements 17 are not in contact with the heart wall and are in the non-contact mode.

The imaging apparatus 12 generates at least one image of the sensing apparatus within the object 2 and this image is used by the registration unit 58 for registering a model of the object 2 with the sensing apparatus within the object 2 in step 103. In step 104 the electrical signals are processed, i.e. the processing unit 57 processes the electrical signals detected by the electrical signal detection unit 51 by applying a non-contact filter to the acquired electrical signals and the electrical signal transforming unit 56 transforms the far-field electrical signals onto a surface of the object. Thus, the electrical signals, in particular, electrograms, are determined on the surface of the object.

In step 105, the analysis unit 60 determines regions comprising an abnormal behavior, in particular, an abnormal electrogram, by using the transformed far field electrical signals and the display unit 61 displays the model of the object 2 and at least the regions comprising the abnormal behavior, in particular, the abnormal electrograms, on the model in step 106.

In step 107, the arrangement 7 of sensing elements 17 is moved to a region comprising an abnormal behavior, in particular, an abnormal electrogram, indicated on the display unit 61 by using the steering unit 62. In step 108, if the sensing elements 17 are in contact with a surface of the object 2, which is preferentially detected by the mode determination unit 55, electrical signals are acquired by the sensing elements 17 in the contact mode by using a bipolar acquisition. In step 109, the sensing elements 17 are registered with the model of the object 2 by using a further image of the imaging apparatus 12, and in step 110 the electrical signal processing unit 57 applies a contact-mode filter on the acquired electrical signals and, in particular, generates a map of electrograms, which is shown on the model of the object 2 on the display unit 61. Furthermore, in step 110, the analysis unit 60 determines preferentially which regions have an abnormal electrical behavior, in particular, an abnormal electrogram, based on the processed electrical signals acquired in the contact mode, wherein the result of this analysis is preferentially also displayed on the display.

In step 111, it is determined whether a stopping criterion is fulfilled for stopping the sensing method or not. If the stopping criterion is fulfilled, the sensing method ends in step 112. Otherwise, the sensing method continuous with step 107 with another region comprising an abnormal electrical behavior, in particular, an abnormal electrogram.

According to a preferred stopping criterion the sensing method is stopped if all regions comprising an abnormal electrical behavior, in particular, an abnormal electrogram, have been sensed in the contact mode. Preferentially, the sensing method is also stopped if a user enters a corresponding signal into the sensing apparatus, for example, by entering a corresponding signal in the control unit 5 via, for example, an input unit like a keyboard or a mouse.

In another embodiment, a user can decide in step 111 whether the sensing method should continue with step 101 or with step 107, i.e. a user can decide whether a sensing in a non-contact mode should be performed before performing the next contact mode sensing.

Atrial fibrillation (AF) is a common cardiac arrhythmia characterized by chaotic electrical activity and a deterioration of the mechanical function of the atria. As a result of impaired hemodynamics (a lack of synchronized atrial contraction, blood stasis in the atria, and impaired ventricular function), AF is associated with a significant increase in morbidity and mortality from stroke, heart failure, and dementia. AF is driven by sites within the atria that are patient-specific and characterized by abnormal local electrical measurements (electrograms).

Known electrogram-based mapping systems sense patient-specific data of cardiac electrical activity. These systems (e.g. the Biosense-Webster CARTO mapping catheter) use a single-point sensor to sequentially acquire contact electrograms over the entire internal surface of the atria. This data is mapped to a 3D electro-anatomical model of the heart. Because mapping is done point-by-point, precise localization of patient-specific drivers of the AF is a time-consuming process. As a result, even though it is recognized as a successful therapy for AF, patient-specific mapping and ablation is usually not conducted. Instead, since these sites often reside close to known anatomical regions, treatment involves ablating wide anatomical regions (in the hope of electrically isolating pro-arrhythmic sites) instead of finding and eliminating the target sites themselves. Because of this, catheter ablation therapy in these patients using known devices and methods has limited efficacy and efficiency.

Localization of patient-specific drivers of AF requires a high-density, accurate mapping of the endocardial surface. As mentioned above, point-to-point mapping tools such as CARTO and NavX are most commonly used to do this. The Ensite Array (St Jude) can detect in real-time the atrial activation pattern and localize areas of early activation by a multipoint sensing catheter used in non-contact mode. However, this system does not achieve the accuracy required for mapping patient-specific drivers of AF, therefore is rarely used. Common to all these mapping technologies is the use of proprietary methods for catheter localization i.e. the imaging modalities already used for image guidance in minimally-invasive interventions are not used.

The sensing apparatus in accordance with the present invention improves the efficiency and accuracy of finding regions with abnormal electrical behavior, in particular, with abnormal electrograms, and of analyzing these regions.

Although in the above described embodiment the object is preferentially a heart of a patient, the invention is not limited to the application on a heart of a patient. In other embodiments, the sensing apparatus can be adapted to sense another object like another organ or a technical object.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Calculations, like the registration, filtering, transforming etc., performed by one or several units or devices can be performed by any other number of units or devices. For example, the steps 102 to 105 and 109 to 111 can be performed by a single unit of by any other number of different units. The calculations and/or the control of the sensing apparatus in accordance with the sensing method can be implemented as program code means of a computer program and/or as dedicated hardware.

A computer program may be stored/distributed on a suitable medium, such as an optical storage medium or a solidstate medium, supplied together with or as part of other hardware, but may also be distributed in other forms, such as via the Internet or other wired or wireless telecommunication systems.

Any reference signs in the claims should not be construed as limiting the scope.

The invention claimed is:

1. A sensing apparatus for sensing an object, comprising:
   an arrangement of sensing elements for sensing a property of the object and acquiring electrical signals, wherein the sensing elements are operable in a contact mode, in which a sensing is performable, while the sensing elements are in contact with the object, and in a non-contact mode, in which a sensing is performable, while the sensing elements are not in contact with the object; and
   an electrical signal processing unit configured to perform both a non-contact mode filtering of the electrical signals to retain only frequencies in a first range if the sensing elements are in the non-contact mode, and to perform a contact mode filtering of the electrical signals to retain only frequencies in a second range if the sensing elements are in the contact mode, wherein the first range is different from the second range.

2. The sensing apparatus as claimed in claim 1, further comprising a mode determination unit for determining whether a sensing element is in contact with the object not.

3. The sensing apparatus as claimed in claim 1 further comprising a detection unit, wherein the sensing elements are adapted to acquire an electrical signal, which depends on the property to be determined, by performing a unipolar acquisition by the detection unit, if the sensing elements are in the non-contact mode, and to acquire an electrical signal, which depends on the electrical potential, by performing a unipolar or bipolar acquisition by the detection unit, if the sensing elements are in the contact mode.

4. The sensing apparatus as claimed in claim 1, further comprising a tube for containing at least the arrangement of sensing elements for guiding the sensing elements in the interior of the object for sensing the interior of the object.

5. The sensing apparatus as claimed in claim 1, further comprising a holding structure for holding the arrangement of sensing elements, wherein the sensing elements are arranged on the holding structure, wherein the holding structure is adjustable between a folded condition and at least one unfolded condition and wherein the holding structure comprises an elongated shape in the folded condition.

6. The sensing apparatus as claimed in claim 5, wherein the holding structure is adapted such and the sensing elements are arranged such that the spacing between the sensing elements in a first unfolded condition is different to the spacing between the sensing elements in a second unfolded condition.

7. The sensing apparatus as claimed in claim 1, wherein the sensing elements are adapted to apply energy and to receive energy.

8. The sensing apparatus as claimed in claim 1, further comprising markers for being visualized in an imaging apparatus.

9. The sensing apparatus as claimed in claim 8, further comprising a registering unit for registering the sensing elements and a model of the object.

10. The sensing apparatus of claim 1, wherein the first range is from 0.1 to 300 Hz and the second range is from 30 to 500 Hz.

11. The sensing apparatus of claim 1, wherein the first range is from 1 to 200 Hz and the second range is from 100 to 400 Hz.

12. The sensing apparatus of claim 1, wherein the first range is from 50 to 150 Hz and the second range is from 200 to 300 Hz.

* * * * *